United States Patent [19]

Dickens et al.

[11] Patent Number: 4,599,361

[45] Date of Patent: Jul. 8, 1986

[54] HYDROXAMIC ACID BASED COLLAGENASE INHIBITORS

[75] Inventors: Jonathan P. Dickens; David K. Donald, both of High Wycombe; Geoffrey Kneen, West Wycombe; William R. McKay, High Wycombe, all of England

[73] Assignee: G. D. Searle & Co., Skokie, Ill.

[21] Appl. No.: 774,491

[22] Filed: Sep. 10, 1985

[51] Int. Cl.$^4$ .................. C07C 83/10; A61K 31/085; A61K 31/165; A61K 31/185
[52] U.S. Cl. ............................. 514/575; 260/500.5 H
[58] Field of Search ................. 260/500.5 H; 514/575

[56] References Cited

U.S. PATENT DOCUMENTS

| | | | |
|---|---|---|---|
| 3,247,197 | 4/1966 | Gaeumann et al. | 260/500.5 H |
| 3,471,476 | 10/1969 | Gaeumann et al. | 260/500.5 H |
| 4,028,401 | 6/1977 | Fessler et al. | 260/500.5 H |
| 4,077,998 | 3/1978 | Fessler et al. | 260/500.5 H |
| 4,105,789 | 8/1978 | Ondetti et al. | 260/500.5 H |
| 4,397,867 | 8/1983 | Blake | 514/575 |
| 4,419,365 | 12/1983 | McLachlan | 514/575 |

*Primary Examiner*—J. E. Evans
*Attorney, Agent, or Firm*—Steven M. Odre

[57] ABSTRACT

This disclosure relates to a novel class of hydroxamic acid based collagenase inhibitor derivatives. The disclosure further relates to pharmaceutical compositions containing such compounds and to the use of such compounds and compositions in the treatment of collagenase induced diseases.

11 Claims, No Drawings

HYDROXAMIC ACID BASED COLLAGENASE INHIBITORS

This invention relates to a novel class of hydroxamic acid based collagenase inhibitor derivatives. The present invention further relates to pharmaceutical compositions containing such compounds and to the use of such compounds and compositions in the treatment of collagenase induced diseases.

BACKGROUND OF THE INVENTION

A number of compounds have been described which are competitive reversible inhibitors of zinc-containing metalloproteinase enzymes. Such competitive reversible inhibitors include for example inhibitors of the angiotensin converting enzymes (ACE). Such an inhibitor acts to block conversion of the decapeptide angiotensin I to angiotensin II a potent pressor substance. ACE inhibitors are of use in the treatment of hypertension. Compounds of this type are for example described in European Patent Application A-0012401. Related inhibitors of the enzyme enkephalinase are described in EPA 0054862.

The compounds of the present invention act as inhibitors of mammalian collagenase [EC 3.4.24.7] which initiates collagen breakdown. There is evidence (for example *Arthritis and Rheumatism*, 20, 1231–1239, 1977) implicating the involvement of the zinc metalloproteinase, collagenase, as one of the key enzymes in the degradation of articular cartilage and bone in rheumatoid arthritis. Collagen is one of the major components of the protein matrix of cartilage and bone. Potent inhibitors of collagenase are useful in the treatment of rheumatoid arthritis and associated diseases in which collagenolytic activity is a contributing factor. These diseases include corneal ulceration, osteoporosis, periodontitis, gingivitis, tumour invasion and dystrophic epidermolysis bullosa.

U.S. Pat. No. 4,511,504 describes a class of novel carboxyalkyl peptide derivatives which are useful as collagenase inhibitors. U.S. application Ser. No. 06/703,973, filed Feb. 2, 1985, describes a class of thiol based collagenase inhibitors which are useful in the treatment of diseases in which collagenase promoted collagen breakdown is a causative factor.

SUMMARY OF THE INVENTION

The present invention relates to a novel class of compounds of the formula $$\underset{a}{\overset{O}{\overset{\|}{HOHNC}}-A-\overset{O}{\overset{\|}{CNH}}-\overset{R^2}{\underset{|}{CH}}-\overset{O}{\overset{\|}{CNHR^1}}} \quad (I)$$

wherein
$R^1$ is $C_1$–$C_6$ alkyl;
$R^2$ is $C_1$–$C_6$ alkyl, benzyl, benzyloxybenzyl, ($C_1$–$C_6$ alkoxy)benzyl or benzyloxy($C_1$–$C_6$ alkyl);
a is a chiral center with optional R or S stereochemistry;
A is a

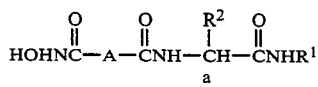

or a —($CR^3$=$CR^4$)— group wherein b and c are chiral centers with optional R or S stereochemistry; $R^3$ is hydrogen, $C_1$–$C_6$ alkyl, phenyl or phenyl($C_1$–$C_6$ alkyl) and $R^4$ is hydrogen, $C_1$–$C_6$ alkyl, phenyl(-$C_1$–$C_6$ alkyl), cycloalkyl or cycloalkyl($C_1$–$C_6$ alkyl).

DETAILED DESCRIPTION

This invention relates to the above-described novel compounds having pharmacological activity, to the production thereof, to compositions containing them, and to their use in the treatment or management of conditions or diseases, e.g., rheumatoid arthritis, in which collagenase promoted collagen breakdown is a causative factor.

As used herein, the term "$C_1$–$C_6$ alkyl" refers to a straight or branched chain alkyl moiety having from 1 to 6 carbon atoms, including for example, methyl, ethyl, propyl, isopropyl, butyl, t-butyl, pentyl, hexyl and the like.

The term "$C_1$–$C_6$ alkoxy" refers to a straight or branched chain alkyl moiety having from 1 to 6 carbon atoms, including for example, methoxy, ethoxy, propoxy, butoxy, t-butoxy, pentoxy, hexoxy and the like.

The term "cycloalkyl" refers to a saturated alicyclic moiety having from 4 to 8 carbon atoms, including for example, cyclobutyl, cyclopentyl, cyclohexyl and the like.

There are several chiral centers in the compounds according to the invention because of the presence of asymmetric carbon atoms.

According to the invention, the presence of several asymmetric carbon atoms gives rise to diastereomers with the appropriate R or S stereochemistry at each chiral center. The invention is understood to include all such diastereomers and mixtures thereof.

A preferred embodiment of the present invention includes compounds of the formula

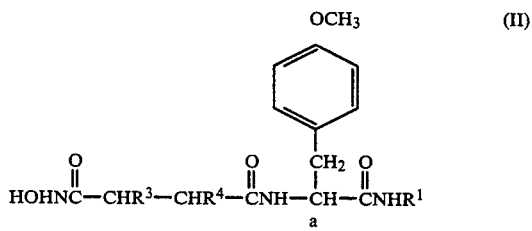

wherein $R^3$ and $R^4$ are above defined and chiral center a is S stereochemistry. A more preferred embodiment of the present invention includes compounds of formula (II) wherein $R^4$ is 2-methylpropyl.

The compounds according to the invention may be made by methods which are generally known in peptide chemistry for analogous compounds. In particular it is to be understood that reactive groups not involved in a particular reaction (e.g. amino, carboxy, hydroxy, etc.,) may be protected by methods standard in peptide chemistry prior to reactions of other groups and subsequently deprotected.

The compounds of the present invention wherein A is a

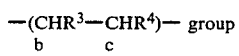

may be prepared in accordance with the following general procedure:

A substituted acid of the formula

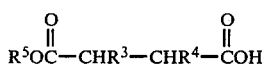

wherein $R^3$ and $R^4$ are above defined and $R^5$ is $C_1$-$C_6$ alkyl or benzyl; is coupled to an amide of the formula

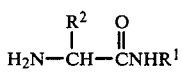

wherein $R^1$ and $R^2$ are above defined; in the presence of a coupling agent such as N,N'-dicyclohexyl carbodiimide to yield a compound of the formula

The compounds of formula (V) are hydrolyzed in the presence of a base such as sodium hydroxide or hydrogenated in the presence of a catalyst to yield the corresponding acid of the formula

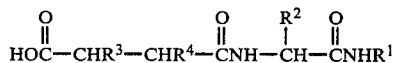

The acid of formula (VI) is converted to the hydroxamic acid derivative of formula (I) by coupling the acid with O-benzylhydroxylamine followed by hydrogenation or alternatively by coupling the acid directly with hydroxylamine using a coupling agent such as ethyl chloroformate. If desired, the products of formula (I) may be separated into the individual isomers by chromatography.

The starting materials and reagents employed in the above general procedure are generally commercially available or may be prepared in accordance with standard techniques. For example, the substituted acid of formula (III) may be prepared by reacting an ester of the formula

wherein $Y^1$ is halo, and $R^3$ and $R^5$ are above defined; with triethylphosphite to yield a compound of the formula

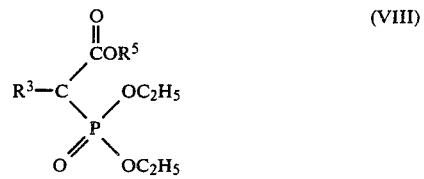

The compound of formula (VIII) is reacted with a keto acid ester of the formula

wherein $R^6$ is a protecting group such as benzyl and $R^4$ is above defined; and sodium hydride or other suitable base in the presence of an appropriate solvent, such as toluene, to yield a compound of the formula

The compounds of formula (X) wherein $R^5$ is $C_1$-$C_6$ alkyl are hydrogenated to yield the compounds of formula (III).

In addition the compounds of formula (VI) may be prepared upon reaction of an acid of the formula

with an amide of formula (IV) in the presence of an amide bond coupling agent, such as N,N'-dicyclohexyl carbodiimide, to yield a compound of the formula

The compounds of formula (XII) are reacted with a compound of formula (VIII) in the presence of a base, such as potassium t-butoxide in dimethylformamide to yield a compound of the formula

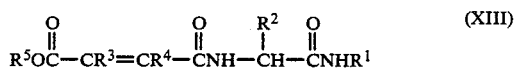

The compounds of formula (XIII) wherein $R^5$ is benzyl are hydrogenated to yield the compounds of formula (VI).

The compounds of formula (I) wherein A is a —($CR^3$=$CR^4$)— group may be prepared in accordance with the following procedure:

A compound of the formula (XIII) wherein $R^5$ is benzyl is deprotected by transfer hydrogenation using cyclohexene and palladium on carbon in a suitable solvent such as ethanol to yield an acid of the formula

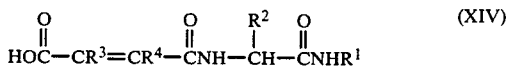

The acid of formula (XIV) is coupled with O-benzyl hydroxylamine followed by hydrogenation or alternatively coupled with hydroxylamine using a coupling agent such as ethyl chloroformate, to yield the compound of the formula

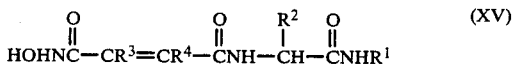

In addition, it should be noted that when A is a —CR³=CR⁴— both the cis and trans isomers are included within the scope of the invention.

The compounds of the invention act as inhibitors of mammalian collagenase which initiates collagen breakdown. Extensive proteolytic enzyme-promoted degradation of articular cartilage and bone is associated with joint destruction in rheumatoid arthritis. Collagen is one of the major components of the protein matrix of joint cartilage and bone. Histological observations of rheumatoid lesions have established that such lesions are characterized by the proliferation of synovial lining cells with subsequent neovascularization and infiltration by plasma cells, macrophages and T-lymphocytes, collectively referred to as soft tissue or "pannus". The importance of such soft tissue in cartilage erosion has been well demonstrated.

Evanson and coworkers, for example, found that large amounts of neutral collagenase are produced by pannus tissue (Evanson, J. M., et al., *J. Clin. Invest.*, 47, 2639–2651, 1968). More recently, others have confirmed that neutral collagenase plays an important degradative role in the arthritic joints of experimental animals (see Cambray, et al., *Rheumatol Int.* 1, 11–16 and 17–20, 1981) and in humans (Cawston, et al., *Arthritis & Rheum.*, 27, 285–290, 1984).

A mono-specific antiserum to purified synovial collagenase has been used to localize the enzyme in rheumatoid tissues (Wooley, et al., *Eur. J. Biochem.*, 69, 421–428, 1976). Immunoreactive collagenase was detected in high density at the cartilage-pannus junction (Wooley, et al., *Arthritis & Rheumatism*, 20, 1231–1239, 1977) Wooley, et al., (*Science*, 200, 773–775, 1978) have further identified a sub-population of synovial cells responsible for collagenase production.

Thus, the foregoing observations have provided conclusive evidence that collagenase is directly involved in the cartilage erosion process seen in rheumatoid arthritis. Collagenase is also produced by cultured bone tissue (*Vase. Biochem. J.*, 126, 275–289, 1972) and has been implicated in the degradation of the collagenous bone matrix during bone resorption.

Accordingly, the compounds of the present invention which specifically inhibit mammalian collagenase are pharmacologically useful in the treatment of rheumatoid arthritis and related diseases in which collagenolytic activity is contributing factor, such as, for example, corneal ulceration, osteoporosis, periodontitis, Paget's disease, gingivitis, tumor invasion, dystrophic epidermolysis bullosa, systemic ulceration, epidermal ulceration, gastric ulceration and the like.

These compounds have substantially no angiotensin converting enzyme (ACE)-inhibiting activity. ACE is a carboxydipeptidase—it cleaves a peptide substrate two residues from the C-terminus. Consequently the C-terminal carboxylic acid is a prime recognition site for both substrate and inhibitors; removal of this group drastically reduces inhibitory potency. Collagenase, on the other hand, is an endopeptidase and, as such, has no prerequisite for this binding interaction. Additionally, the structure of collagen differs essentially from angiotensin-I which is decapeptide and is cleaved at a phenylalanine-histidine bond to give an octapeptide (angiotensin-II and a dipeptide (histidylleucine)). Collagen is much more complex, in being a triple helix, each strand of the helix containing of the order of 1,000 amino acid residues, the sequence of amino acids around the site cleaved by collagenase being completely different from that around the cleavage site of Angiotensin I. Collagenase cleaves approximately two-thirds of the way along the chain from the N-terminus. The amide bond which is cleaved by collagenase is either a glycine-leucine or a glycine-isoleucine bond.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients. The compounds and composition may for example be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient from about 1 to 250 mg preferably from about 25 to 150 mg. A suitable daily dose for a mammal may vary widely depending on the condition of the patient and other factors. However, a dose of from about 0.1 to 300 mg/kg body weight, particularly from about 1 to 100 mg/kg body weight may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight.

The dosage regimen for treating a disease condition with the compounds and/or compositions of this invention is selected in accordance with a variety of factors, including the type, age, weight, sex and medical condition of the patient; the severity of the infection; the route of administration; and the particular compound employed and thus may vary widely.

For therapeutic purposes, the compounds of this invention are ordinarily combined with one or more adjuvants appropriate to the indicated route of administration. If per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. Appropriate dosages, in any given instance, of course depend upon the nature and severity of the condition treated, the route of administration, and the species of mammal involved, including its size and any individual idiosyncrasies.

Representative carriers, diluents and adjuvants include for example, water, lactose, gelatin, starches, magnesium stearate, talc, vegetable oils, gums, polyalkylene glycols, petroleum jelly, etc. The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

For use in treatment of rheumatoid arthritis the compounds of this invention can be administered by any convenient route preferable in the form of a pharmaceutical composition adapted to such route and in a dose effective for the intended treatment. In the treatment of arthritis administration may conveniently be by the oral route or by injection intra-articularly into the affected joint. The daily dosage for a 70 kilogram mammal will be in the range of 10 milligrams to 1 gram.

As indicated, the dose administered and the treatment regimen will be dependent, for example, on the disease, the severity thereof, on the patient being treated and his response to treatment and therefore may be widely varied.

The following Examples are intended to further illustrate the present invention and not to limit the invention in spirit or scope. In the Examples, all parts are parts by weight unless otherwise expressly set forth.

EXAMPLE 1

N-[3-(N'-Hydroxycarboxamido)-2-(2-methylpropyl)-propanoyl]-O-methyl-L-tyrosine N-Methylamide (a) E and Z Benzyl 3-(ethoxycarbonyl)-2-(2-methylpropyl)propenoate Ethoxycarbonylmethylenetriphenylphosphorane (53.8 g., 0.155 mol.) was dissolved in dry dichloromethane (400 mls.) and the resulting solution was cooled to 0° C. To the cooled solution was added a solution of benzyl 4-methyl-2-oxopentanoate (34.0 g., 0.155 mol.) in dry dichloromethane (100 mls.) over a period of 25 minutes and the reaction mixture was then heated under reflux for 1 hour. The solvent was removed from the reaction mixture by evaporation in vacuo to yield an off-white solid. The solid was extracted with hexane (3×200 mls.) and the solvent was removed from the combined hexane extracts to yield a crude product as a yellow oil. The crude product was purified by distillation (0.6 mm Hg), to yield E and Z benzyl 3-(ethoxycarbonyl)-2-(2-methylpropyl)propenoate (41.0 g.) being collected at 137°–142° C.

(b) 3-(Ethoxycarbonyl)-2-(2-methylpropyl)propanoic acid

E and Z benzyl 3-(ethoxycarbonyl)-2-(2-methylpropyl)propenoate (25.0 g., 0.09 mol.) was dissolved in ethanol and hydrogenated at 50° C. under 37.5 psi in the presence of 5% palladium on charcoal (2.5 g). The resultant mixture was filtered through Celite and the solvent removed by evaporation in vacuo to yield 3-(ethoxycarbonyl)-2-(2-methylpropyl)propanoic acid as a mixture of isomers in the form of a thick oil.

(c) N-[3-(Ethoxycarbonyl)-2-(2-methylpropyl)propanoyl]-O-methyl-L-tyrosine N-Methylamide A mixture of 3-(ethoxycarbonyl)-2-(2-methylpropyl)propanoic acid (17.4 g., 0.087 mol.), N-methylmorpholine (28.7 mls., 0.26 mol.) and dimethylformamide (0.25 ml.) was dissolved in dry dichloromethane (200 mls.) and the resulting mixture was cooled to 0° C. To the reaction mixture was added a solution of oxalyl chloride (7.6 mls., 0.087 mol.) in dry dichloromethane (50 mls.). The mixture was heated under reflux for 10 minutes and then cooled to −70° C. To the reaction mixture was added O-methyl-L-tyrosine N-methylamide (20.0 g., 0.096 mol.) in dry dichloromethane (100 mls.) over a period of 30 minutes. The resulting mixture was allowed to warm to room temperature and stirred for 2.5 days. The mixture was filtered and the filtrate washed with saturated sodium bicarbonate solution (2×200 mls.), dilute citric acid (2×150 mls.) and then dried over anhydrous sodium sulfate. The solvent was then removed by evaporation in vacuo to yield N-[3-(ethoxycarbonyl)-2-(2-methylpropyl)propanoyl]-O-methyl-L-tyrosine N-methylamide, as a mixture of isomers (20.7 g.), in the form of a solid.

(d) N-[3-Carboxy-2-(2-methylpropyl)propanoyl]-O-methyl-L-tyrosine N-Methylamide N-[3-(Ethoxycarbonyl)-2-(2-methylpropyl)-propanoyl]-O-methyl-L-tyrosine N-Methylamide (4.7 g., 0.012 mol.) was suspended in methanol (25 mls.) containing potassium hydroxide solution (12 mls. of 1M). The mixture was stirred overnight and the solvent was removed by evaporation in vacuo to yield a gum. The gum was partitioned between diethyl ether (50 mls.) and sodium bicarbonate solution (50 mls.). The aqueous phase was separated, washed with ethyl ether (50 mls.) and adjusted to pH 2 by the addition of dilute hydrochloric acid. The aqueous mixture was extracted with dichloromethane (3×100 mls.) and the extracts combined and then dried over anhydrous sodium sulfate. The solvent was removed by evaporation in vacuo to yield a gum (3.3 g.). The gum was recrystallized from a mixture of dichloromethane and hexane to yield N-[3-carboxy-2-(2-methylpropyl)propanoyl]-O-methyl-L-tyrosine N-methylamide as a white solid which was a mixture of two diastereomers. (m.p. 92°–96° C. Found: C, 61.7; H, 7.6; N, 7.5%. $C_{19}H_{28}N_2O_5 \cdot 0.3H_2O$ requires C, 61.7; H, 7.8; N, 7.6%).

(e) N-[3-(N'-Hydroxycarboxamido)-2-(2-methylpropyl)-propanoyl]-O-methyl-L-tyrosine N-Methylamide To N-[3-carboxy-2-(2-methylpropyl)propanoyl]-O-methyl-L-tyrosine N-methylamide (0.73 g., 0.002 mol.) dissolved in dry tetrahydrofuran (10 mls.) was added triethylamine (0.24 g.) and the resultant mixture cooled to 0° C. A solution of ethyl chloroformate (0.26 g., 0.0024 mol.) in dry tetrahydrofuran (4 mls.) was added to the reaction mixture which was then stirred for 0.5 hr. at 0° C. and then was allowed to warm to room temperature. Hydroxylamine hydrochloride (0.69 g., 0.01 mol.) was added to the reaction mixture. The resultant mixture was cooled to 0° C. and triethylamine (1.1 g., 0.012 mol.) in dry tetrahydrofuran (2 mls.) was added. The reaction mixture was allowed to warm to room temperature and stirred overnight. The solvent was removed by evaporation in vacuo and the resultant sticky solid taken up in ethyl acetate (50 mls.) The ethyl acetate solution was washed with dilute citric acid (2×4 mls.), dried over anhydrous sodium sulfate and the solvent was removed by evaporation in vacuo to yield a crude product. The crude product was purified by chromatography on normal phase silica eluting with dichloromethane/methanol/acetic acid (43:6:1) to yield N-[3-(N'-hydroxycarboxamido)-2-(2-methylpropyl)-propanoyl]-O-methyl-L-tyrosine N-methylamide as a mixture of diastereomers as a white solid (m.p. 165°–7° C. Found: C, 59.7; H, 7.7; N, 10.7%. $C_{19}H_{29}N_3O_5 \cdot 0.2H_2O$ requires C, 59.6; H, 7.7; N, 11.0%) represented by the general structural formula:

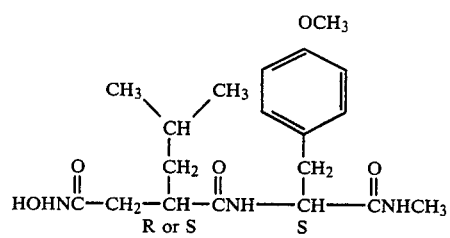

EXAMPLE 2
N-[3-(N'-Hydroxycarboxamido)-2-(2-methylpropyl)-propanoyl]-O-methyl-L-tyrosine N-Methylamide

(a) N-(4-Methyl-2-oxopentanoyl)-O-methyl-L-tyrosine N-Methylamide

4-Methyl-2-oxopentanoic acid (31.3 g., 0.24 mol.) was dissolved in dry dichloromethane (50 mls.) and the resultant solution was cooled to 0° C. To the solution was added dropwise oxalyl chloride (23.2 mls., 0.265 mol.), followed by dimethylformamide (0.5 ml.). The resultant mixture was stirred at 0° C. for 1 hour, and then heated under reflux for 5 minutes and then allowed to cool. O-Methyl-L-tyrosine N-Methylamide (50.0 g., 0.24 mol.) and triethylamine (37.1 mls., 0.265 mol.) were dissolved in dichloromethane (120 mls.) and the resultant solution added dropwise to the cooled reaction mixture. The mixture was allowed to warm to room temperature and stirred overnight. The mixture was poured into water (50 mls.) and the organic layer was removed. The aqueous layer was extracted with dichloromethane (30 mls.), the combined extracts were dried over anhydrous sodium sulfate and the solvent removed by evaporation in vacuo to yield a crude product as a yellow solid (85.1 g.). The crude product was recrystallized from tertiary butyl ethyl ether to yield N-(4-methyl-2-oxopentanoyl)-O-methyl-L-tyrosine N-methylamide (55.6 g.)

(m.p. 152°–8° C. Found: C, 63.2; H, 7.6; N, 8.8%. $C_{17}H_{24}N_2O_4$ requires C, 63.4; H, 7.6; N, 8.7%).

(b) E and Z N-[3-(Benzyloxycarbonyl)-2-(2-methylpropyl)-propenoyl]-O-methyl-L-tyrosine N-Methylamide Potassium tertiary butoxide (2.1 g., 0.0188 mol.) was suspended in dry dimethylformamide (50 mls.). To the suspension was added benzyl dimethylphosphonoethanoate (4.6 g., 0.0187 mol.) at room temperature. The reaction mixture was stirred at room temperature for 0.5 hours. N-(4-Methyl-2-oxopentanoyl)-O-methyl-L-tyrosine N-Methylamide (3.0 g., 0.00913 mol) was added portionwise to the reaction mixture over a period of 10 minutes to yield a red solution. The red solution was stirred at room temperature for 4 hours, and then poured into water (500 mls.). The resulting mixture obtained was extracted with ethyl acetate (2×100 mls.) and the ethyl acetate extract was washed with water (2×25 mls.), brine (25 mls.) and dried over anhydrous magnesium sulfate. The ethyl acetate was removed by evaporation in vacuo to yield a crude solid product (4.2 g.). The crude product was purified by recrystallization from a mixture of ethyl acetate and hexane to yield E and Z N-[3-(benzyloxycarbonyl)-2-(2-methylpropyl)-propenoyl]-O-methyl-L-tyrosine N-methylamide as a light brown crystalline solid. (m.p. 167°–9° C. Found: C, 68.3; H, 7.1; N, 6.3%. $C_{25}H_{30}N_2O_5$ requires C, 68.5; H, 6.9; N, 6.4%).

(c)
N-[3-Carboxy-2-(2-methylpropyl)propanoyl]-O-methyl-L-tyrosine N-Methylamide

E and Z N-[3-(benzyoxycarbonyl)-2-(2-methylpropyl)propenoyl]-O-methyl-L-tyrosine N-methylamide (1.7 g., 0.0039 mol.) was hydrogenated at 50° C. and 60 psi for 5 hours in the presence of methanol (50 mls.) and 10% palladium on charcoal (0.5 g.). The resulting mixture was filtered through Celite and the solvent removed by evaporation in vacuo to yield a diastereomeric mixture of N-[3-carboxy-2-(2-methylpropyl)propanoyl]-O-methyl-L-tyrosine N-methylamide, a colorless solid product (1.4 g.) which was separated by chromatography on normal phase silica to yield isomers A and B represented by the general structural formula:

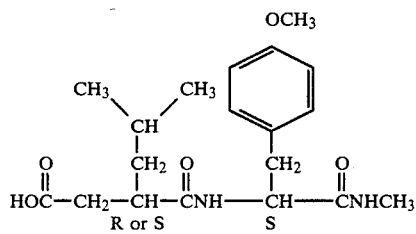

(d)
N-[3-(N'-Hydroxycarboxamido)-2-(2-methylpropyl)-propanoyl]-O-methyl-L-tyrosine N-Methylamide By methods described in Example 1(e) the separated isomers of N-[3-carboxy-2-(2-methylpropyl)-propanoyl]-O-methyl-L-tyrosine N-methylamide were converted to the corresponding hydroxamic acids to yield isomers A and B represented by the general structural formula:

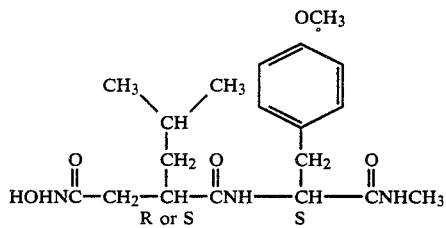

Isomer A (m.p. 190°–195° C. Found: C, 59.5; H, 7.5; N, 10.6%. $C_{19}H_{29}N_3O_5 \cdot 0.2H_2O$ requires C, 59.6; H, 7.5; N, 11.0%).

NMR (d$_6$-DMSO) 0.7–0.9 (6H, m, {CH$_3$}$_2$CH); 1.3 (1H, m, {CH$_3$}$_2$CH); 1.9–2.2 (3H, 2xm, CH$_2$CH); 2.50 (3H, m, CHCH$_2$CO, +CH$_2$CHCO); 2.6 (2H, m, ArCH$_2$); 2.6 (3H, d, NHCH$_3$); 3.7 (3H, s, OCH$_3$); 4.3–4.4 (1H, m, ArCH$_2$CH); 6.75–7.1 (4H, 2xd, J=8 Hz, aromatic); 7.9 (1H, m, NHCH$_3$); 8.05 (1H, d, CONHCH); 8.65 (1H, s, NHOH (D$_2$O exchange)); 10.4 (1H, s, NHOH {D$_2$O exchange}).

Isomer B (m.p. 179°–182° C. Found: C, 57.6; H, 7.8; N, 10.4%. $C_{19}H_{29}N_3O_5 \cdot 0.9H_2O$ requires C, 57.7; H, 7.9; N, 10.6%).

NMR (d$_6$-DMSO) 0.5–0.8 (6H, m, {CH$_3$}$_2$CH); 1.1–1.25 (1H, m, {CH$_3$}$_2$CH); 1.9–2.2 (3H, 2xm, CH$_2$CH); 2.5 (3H, m, CH$_2$CHCO); 2.60 (2H, m, ArCH$_2$); 2.65 (3H, d, NHCH$_3$); 3.70 (3H, s, OCH$_3$), 4.3–4.4 (1H, m, ArCH$_2$CH); 6.8 and 7.15 (4H, 2xd, J=8 Hz, aromatic); 7.9 (1H, m, NHCH$_3$); 8.35 (1H, d, CONHCH); 8.8 (1H, s, NHOH {D$_2$O exchange}); 10.5 (1H, s, NHOH {D$_2$O exchange}).

EXAMPLE 3
N-[3-(N'-Hydroxycarboxamido)-2-(2-methylpropyl)-butanoyl]-O-methyl-L-tyrosine N-Methylamide (a) Ethyl 2-(diethylphosphono)propanoate Ethyl 2-bromopropanoate (30.0 g.) and triethylphosphite (70.0 g.) were heated overnight at 150° C. under an air condenser. The resulting crude mixture was purified by distillation, the ethyl 2-(diethylphosphono)-propanoate was collected at 66°–68° C. at 0.3–0.5 mm.Hg.

(b) E and Z Benzyl 3-(ethoxycarbonyl)-2-(2-methylpropyl)butenoate

Ethyl 2-(diethylphosphono)propanoate (23.9 g.) was added to dry toluene (250 mls.) containing 80% sodium hydride in mineral oil (3.0 g.) at room temperature. The resultant mixture was heated to 50°–60° C. for 5 minutes and then cooled to −30° to −40° C. To the cooled mixture was added benzyl 4-methyl-2-oxopentanoate (20 g.) and the resulting mixture was allowed to warm to room temperature over a period of 1 hour. The toluene solution was washed with dilute citric acid (50 mls.), water (2×50 mls.) and then dried over anhydrous sodium sulfate. The toluene was removed by evaporation in vacuo to yield E and Z benzyl 3-(ethoxycarbonyl)-2-(2-methylpropyl)butenoate as a mixture of isomers in the form of an oil.

(c) 3-(Ethoxycarbonyl)-2-(2-methylpropyl)butanoic acid

E and Z benzyl 3-(ethoxycarbonyl)-2-(2-methylpropyl)butenoate (5.0 g.) was hydrogenated at 120 psi at 60° C. in methanol (50 mls.) in the presence of 10% palladium on charcoal (0.25 g.) for 48 hours. The resultant mixture was filtered through Celite and the solvent removed by evaporation in vacuo to yield 3-(ethoxycarbonyl)-2-(2-methylpropyl)butanoic acid as a mixture of isomers in the form of a thick oil.

(d)
N-[3-(Ethoxycarbonyl)-2-(2-methylpropyl)butanoyl]-O-methyl-L-tyrosine N-Methylamide A mixture of 3-(ethoxycarbonyl)-2-(2-methylpropyl)-butanoic acid (7.5 g., 0.037 mol.) and dichloromethane (70 mls.) was stirred and cooled to 0° C. To the mixture was added dropwise a solution of N,N'-dicyclohexylcarbodiimide (7.6 g., 0.37 mol.) in dichloromethane (20 mls.) and the reaction mixture was allowed to warm to room temperature. A solution of O-methyl-L-tyrosine N-methylamide (7.7 g., 0.037 mol.) in dichloromethane (45 mls.) was added to the reaction mixture and the resulting mixture was stirred overnight at room temperature. A saturated sodium bicarbonate solution (100 mls.) was added to the reaction mixture and the resulting mixture was stirred for an additional hour. The reaction mixture was filtered and the organic layer recovered and then dried on anhydrous sodium sulfate. The solvent was removed by evaporation in vacuo to yield a sticky brown solid. The solid was purified by chromatography on normal phase silica eluting with 20% hexane in ethyl acetate to yield N-[3-(ethoxycarbonyl)-2-(2-methylpropyl)butanoyl]-O-methyl-L-tyrosine N-methylamide as a mixture of 4 diastereomers.

(e)
N-[3-Carboxy-2-(2-methylpropyl)butanoyl]-O-methyl-L-tyrosine N-Methylamide

N-[3-(Ethoxycarbonyl)-2-(2-methylpropyl)-butanoyl]-O-methyl-L-tyrosine N-Methylamide (2.0 g., 0.0051 mol.) was hydrolysed upon the addition of 0.1M sodium hydroxide solution (6 mls., 0.006 mol.) in methanol (30 mls.). The solvent was removed by evaporation in vacuo and the resulting gum washed with diethyl ether (2×25 mls.). The gum was acidified with 0.1M hydrochloric acid solution and the mixture was extracted with dichloromethane (2×50 mls.). The combined extracts were dried over anhydrous sodium sulfate and the solvent was removed by evaporation in vacuo to yield N-[3-carboxy-2-(2-methylpropyl)-butanoyl]-O-methyl-L-tyrosine N-methylamide as a mixture of isomers as an off-white solid (1.9 g., 0.0052 mol.).

(f)
N-[3-(N'-Hydroxycarboxamido)-2-(2-methylpropyl)-butanoyl]-O-methyl-L-tyrosine N-Methylamide The mixture of isomers of N-[3-carboxy-2-(2-methylpropyl)butanoyl]-O-methyl-L-tyrosine N-methylamide (1.5 g., 0.0041 mol.), O-benzylhydroxylamine hydrochloride (0.09 g., 0.0061 mol.), N-ethyl-N'-(3-dimethylaminopropyl)carbodiimide hydrochloride (1.17 g., 0.0061 mol.) were stirred overnight in tetrahydrofuran (10 mls.) and water (10 mls.) at room temperature. The solvent was removed by evaporation in vacuo to yield a yellow gum which was partitioned between dichloromethane (50 mls.) and dilute sodium bicarbonate solution (50 mls.). The organic phase was washed with dilute citric acid (25 mls.) and dried over anhydrous sodium sulfate. The solvent was removed by evaporation in vacuo to yield a mixture of the 4 diastereomers of the O-benzylhydroxamic acid in the form of a gum. The mixture was dissolved in ethanol (20 mls.) with cyclohexane (15 mls.) and 10% palladium on charcoal (150 mg.) and the resulting mixture was heated under reflux for 10 minutes. The mixture was filtered through Celite and the solvent was removed by evaporation in vacuo to yield 4 diastereomers of N-[3-(N'-hydroxycarboxamido)-2-(2-methylpropyl)butanoyl]-O-methyl-L-tyrosine N-methylamide as an off-white solid represented by the structural formula:

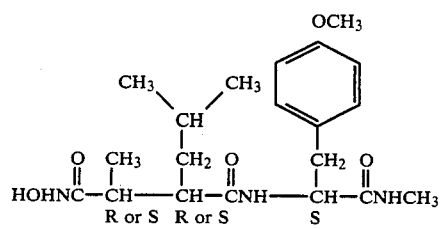

The mixture of isomers was separated by two operations of column chromatography on normal phase silica eluting in the first column with 5% methanol in ethyl acetate and in the second column with dichloromethane/methanol/acetic acid/hexane (20:5:1.5:20).

The 4 isomers were designated as isomers A, B, C and D to describe the order of elution off the column.

Isomer A (m.p. 158°–162° C. Found: C, 58.4; H, 7.6; N, 10.3%. $C_{20}H_{31}N_3O_5$ requires C, 58.4; H, 8.1; N, 10.2%).

NMR ($d_6$-DMSO) 0.53–0.71 (6H, m, {C$\underline{H}_3$}$_2$CH); 0.73 (1H, m, {CH$_3$}$_2$C$\underline{H}$); 0.82 (2H, m, CHC$\underline{H}_2$CH); 1.02 (3H, d, J=7 Hz, C$\underline{H}_3$CH); 2.15 (1H, m, CH$_3$C$\underline{H}$); 2.31 (1H, m, CH$_3$CHC$\underline{H}$); 2.55 (2H, m, ArC$\underline{H}_2$); 2.65 (3H, d, J=5 Hz, NHC$\underline{H}_3$); 3.71 (3H, s, OC$\underline{H}_3$); 4.30 (1H, m, ArCH$_2$C$\underline{H}$); 6.80 and 7.12 (4H, two d's, J=8 Hz, aromatic); 7.51 (1H, m, N$\underline{H}$CH$_3$); 8.36 (1H, d, J=8 Hz, CON$\underline{H}$CH); 8.84 (1H, s, N$\underline{H}$OH {D$_2$O exchange}); 10.68 (1H, s, NHO$\underline{H}${D$_2$O exchange}).

Isomer B (m.p. 168°–174° C. Found: accurate mass 394.2359. $C_{20}H_{31}N_3O_5$ (M+1) requires 394.2342).

NMR ($d_6$-DMSO) 0.72–0.90 (7H, m, {C$\underline{H}_3$}$_2$C$\underline{H}$); 1.05 (2H, m, CHC$\underline{H}_2$CH); 1.45 (3H, m, C$\underline{H}_3$C$\underline{H}$); 2.15 (1H, m, CH$_3$C$\underline{H}$); 2.44 (1H, m, CH$_3$CHC$\underline{H}$); 2.58 (2H, M, ArC$\underline{H}_2$); 2.64 (3H, d, J=4 Hz, NHC$\underline{H}_3$); 3.71 (3H, s. OC$\underline{H}_3$); 4.26 (1H, m, ArCH$_2$C$\underline{H}$); 6.82 and 7.16 (4H, two d's, J=7 Hz, aromatic); 7.25 (1H, m, N$\underline{H}$CH$_3$); 8.26 (1H, d, J=7 Hz, CON$\underline{H}$CH); 8.83 (1H, s, N$\underline{H}$OH {D$_2$O exchange}); 10.64 (1H, s, NHO$\underline{H}$ {D$_2$O exchange}).

Isomer C (m.p. 179°–184° C. Found: accurate mass 394.2359. $C_{20}H_{31}N_3O_5$ (M+1) requires 394.2342).

NMR ($d_6$-DMSO) 0.64–0.92 (9H, m, {C$\underline{H}_3$}$_2$CHC$\underline{H}_2$); 1.30 (3H, m, C$\underline{H}_3$CH); 2.20–2.40 (2H, m, CH$_3$C$\underline{H}$ and CH$_3$CHC$\underline{H}$); 2.45 (2H, m, ArC$\underline{H}_2$); 2.55 (3H, d, J=4 Hz, NHC$\underline{H}_3$); 3.68 (3H, s, OC$\underline{H}_3$); 4.45 (1H, m, AC$\underline{H}_2$C$\underline{H}$); 6.80 and 7.16 (4H, two d's, J=7 Hz, aromatic); 7.72 (1H, m, N$\underline{H}$CH$_3$); 8.18 (1H, d, J=7 Hz, CON$\underline{H}$CH$_3$); 8.72 (1H, s, N$\underline{H}$OH {D$_2$O exchange}); 10.37 (1H, s, NHO$\underline{H}$ {D$_2$O exchange}).

Isomer D (m.p. 215°–220° C. Found: C, 60.7; H, 7.9; N, 10.4%. $C_{20}H_{31}N_3O_5$ requires C, 61.0; H, 7.9; N, 10.7%).

NMR ($d_6$-DMSO) 0.52–0.70 (7H, m, }CH$_3$}$_2$C$\underline{H}$); 0.72 (2H, m, CHC$\underline{H}_2$CH); 0.90 (3H, d, J=6 Hz, C$\underline{H}_3$CH); 2.08 (1H, m, CH$_3$C$\underline{H}$); 2.40 (1H, m, CH$_3$CHC$\underline{H}$); 2.50–2.90 (2H, m, ArC$\underline{H}_2$); 2.60 (3H, d, J=4 Hz, NHC$\underline{H}_3$); 3.70 (3H, s, OC$\underline{H}_3$); 4.45 (1H, m, ArCH$_2$C$\underline{H}$); 6.80 and 7.17 (4H, two d's, J=7 Hz, aromatic); 7.90 (1H, m, N$\underline{H}$CH$_3$); 8.28 (1H, d, J=8 Hz, CON$\underline{H}$CH); 8.75 (1H, s, N$\underline{H}$OH {D$_2$O exchange}); 10.46 (1H, s, NHO$\underline{H}$ {D$_2$O exchange}).

EXAMPLES 4–6

The following compounds were prepared in accordance with the procedures employed in Example 3 using appropriate starting materials:

EXAMPLE 4

N-[3-(N'-Hydroxycarboxamido)-2-(2-methylpropyl)-3-phenylpropanoyl]-O-methyl-L-tyrosine N-Methylamide, represented by the general structural formula:

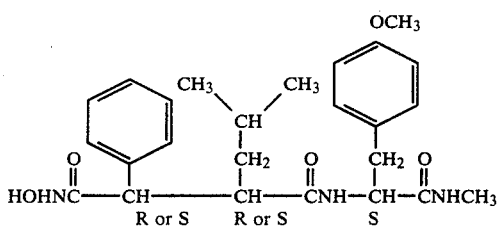

Isomer A (m.p. 196°–200° C. Found: C, 65.5; H, 7.3; N, 9.1%. $C_{25}H_{33}N_3O_5 \cdot 0.2H_2O$ requires C, 65.4; H, 7.3; N, 9.1%).

Isomer B (m.p. 179°–182° C. Found: C, 65.0; H, 7.4; N, 8.7%. $C_{25}H_{33}N_3O_5 \cdot 0.5H_2O$ requires C, 64.6; H, 7.4; N, 9.1%).

EXAMPLE 5

N-[3-(N'-Hydroxycarboxamido)-2-methylpropanoyl]-O-methyl-L-tyrosine N-Methylamide, represented by the general structural formula:

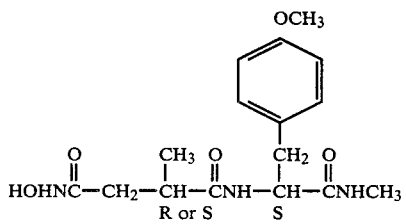

(m.p. 184° C. Found: accurate mass 338.1723. $C_{16}H_{24}N_3O_5$ (M+1) requires 338.1716).

EXAMPLE 6

N-[3-(N'-Hydroxycarboxamido)propanoyl]-O-methyl-L-tyrosine N-Methylamide, represented by the general structural formula:

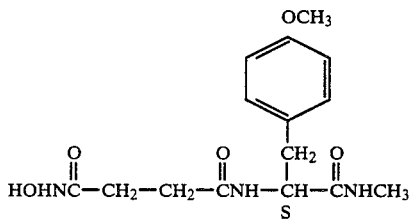

(m.p. 213° C. Found: accurate mass 324.1559. $C_{15}H_{22}N_3O_5$ (M+1) requires 324.1559).

EXAMPLE 7

N-[3-(N'-Hydroxycarboxamido)-2-(2-methylpropyl)-propenoyl]-O-methyl-L-tyrosine N-Methylamide (a) E and Z N-[3-Carboxy-2-(2-methylpropyl)propenoyl]-O-methyl-L-tyrosine N-Methylamide E and Z N-[3-(benzyloxycarbonyl)-2-(2-methylpropyl)propenoyl]-O-methyl-L-tyrosine N-methylamide (3.0 g.) was heated under reflux for 2 hours in ethanol (60 mls.) and cyclohexene (30 mls.) in the presence of 10% palladium on charcoal (0.75 g.). The resultant reaction mixture was filtered through Celite and the solvent removed by evaporation in vacuo to yield a gum. This gum was crystallized from methanol/water to yield E and Z N-[3-carboxy-2-(2-methylpropyl)-propenoyl]-O-methyl-L-tyrosine N-methylamide.

(b) N-[3-(N'-Hydroxycarboxamido)-2-(2-methylpropyl)-propenoyl]-O-methyl-L-tyrosine N-Methylamide E and Z N-[3-Carboxy-2-(2-methylpropyl)-propenoyl]-O-methyl-L-tyrosine N-methylamide (0.2 g., 0.00055 mol.) was dissolved in a mixture of water (3 mls.) and dimethylformamide (5 mls.). O-Benzylhydroxylamine hydrochloride (0.137 g., 0.00083 mol.) was added to the mixture. To the resultant mixture was added N-ethyl-N'-(3-dimethylaminopropyl)carbodiimide hydrochloride (0.164 g., 0.00083 mol.) and the pH of the mixture was adjusted to 4.5 upon addition of 2M sodium hydroxide solution. The mixture was stirred for 1 hour at room temperature and was extracted with ethyl acetate (3×25 mls.). The combined ethyl acetate extracts were washed with dilute citric acid (25 mls.), saturated sodium bicarbonate solution (2×15 mls.) and brine (25 mls.) and then dried over anhydrous sodium sulfate. The solvent was removed by evaporation in vacuo to yield a white solid (0.22 g.). The solid was heated under reflux for a period of 30 minutes in a mixture of ethanol (8 mls.), cyclohexene (4 mls.) and 10% palladium on charcoal (200 mg.). The reaction mixture was filtered through Celite and the solvent removed by evaporation in vacuo to yield a colorless solid. The solid was purified by reverse phase chromatography eluting with 60% methanol in water to yield N-[3-(N'-hydroxycarboxamido)-2-(2-methylpropyl)propenoyl]-O-methyl-L-tyrosine N-methylamide. (m.p. 183°–187° C. Found: C, 60.9; H, 7.6; N, 10.8%. $C_{19}H_{27}N_3O_5$ requires C, 60.5; H, 7.2; N, 11.1%) represented by the general structural formula

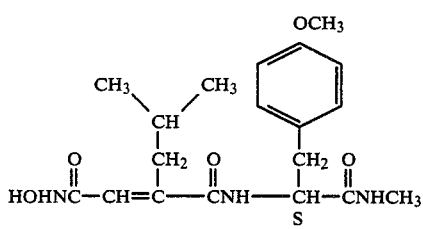

The compounds according to the invention exhibit inhibitory action against collagenase. This was determined following the procedure of Cawston and Barrett, (*Anal. Biochem.*, 99, 340–345, 1979) whereby a 1 mM solution of the inhibitor being tested or dilutions thereof is incubated at 37° C. for 16 hours with native collagen and collagenase (buffered with Tris HCl-CaCl$_2$; pH 7.6). The collagen is acetyl $^{14}$C collagen. The samples are centrifuged to sediment undigested collagen and an aliquot of the radioactive supernatant removed for assay on a scintillation counter as a measure of hydrolysis. The collagenase activity in the presence of 1 mM inhibitor, or a dilution thereof, is compared to activity in a control devoid of inhibitor and the results reported as that inhibitor concentration effecting 50% inhibition of the collagenase. Table I illustrates the activity of compounds of this invention.

TABLE 1

| COLLAGENASE INHIBITION | |
|---|---|
| Example No. (Isomer) | IC$_{50}$ (μM) Human Rheumatoid Synovial Collagenase |
| 1 | 0.1 |
| 2(A) | 0.02 |
| 2(B) | 4.0 |
| 3(A) | 0.4 |
| 3(B) | 20.0 |
| 3(C) | 0.02 |
| 3(D) | 0.3 |
| 4(A) | 0.6 |
| 4(B) | 1.0 |
| 5 | 100–1000 |
| 6 | >1000 |
| 7 | 0.7 |

Although this invention has been described with respect to specific modification, the details thereof are not to be construed as limitations, for it will be apparent that various equivalents, changes and modifications may be restored and modification may be resorted to without departing from the spirit and scope thereof and it is understood that such equivalent embodiments are intended to be included therein.

What is claimed is:

1. A compound of the formula

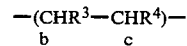

wherein
R$^1$ is C$_1$–C$_6$ alkyl;
R$^2$ is C$_1$–C$_6$ alkyl, benzyl, benzyloxybenzyl, (C$_1$–C$_6$ alkoxy)benzyl or benzyloxy(C$_1$–C$_6$ alkyl);
a is a chiral center with optional R or S stereochemistry;
A is a

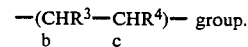

group or a —(CR$^3$=CR$^4$)— group wherein b and c are chiral centers with optional R or S stereochemistry; R$^3$ is hydrogen, C$_1$–C$_6$ alkyl, phenyl or phenyl(C$_1$–C$_6$ alkyl) and R$^4$ is hydrogen or C$_1$–C$_6$ alkyl, phenyl(C$_1$–C$_6$ alkyl), cycloalkyl or cycloalkyl(C$_1$–C$_6$ alkyl).

2. A compound according to claim 1 wherein chiral center a has S stereochemistry.

3. A compound according to claim 2 wherein A is a

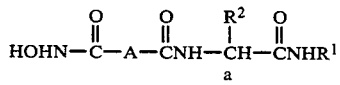

group.

4. A compound according to claim 3 wherein R$^2$ is (C$_1$–C$_6$ alkoxy)benzyl.

5. A compound according to claim 4 wherein R$^2$ is 4-methoxybenzyl, R$^4$ is C$_1$–C$_4$ alkyl and R$^3$ is hydrogen, C$_1$–C$_4$ alkyl, phenyl or phenyl(C$_1$–C$_6$ alkyl).

6. A compound according to claim 5 wherein R$^1$ is methyl, R$^3$ is hydrogen or methyl and R$^4$ is 2-methylpropyl.

7. A compound according to claim 6 wherein R$^3$ is hydrogen.

8. A compound according to claim 7 having the following NMR spectrum:
NMR (d$_6$-DMSO) 0.7–0.9 (6H, m, {CH$_3$}$_2$CH); 1.3 (1H, m, {CH$_3$}$_2$CH); 1.9–2.2 (3H, 2xm, CH$_2$CH); 2.50 (3H, m, CHCH$_2$CO, +CH$_2$CHCO); 2.6 (2H, m, ArCH$_2$); 2.6 (3H, d, NHCH$_3$); 3.7 (3H, s, OCH$_3$); 4.3–4.4 (1H, m, ArCH$_3$CH); 6.75–7.1 (4H, 2xd, J=8 Hz, aromatic); 7.9 (1H, m, NHCH$_3$); 8.05 (1H, d, CONHCH); 8.65 (1H, s, NHOH {D$_2$O exchange}); 10.4 (1H, s, NHOH {D$_2$O exchange}).

9. A compound according to claim 6 wherein R$^3$ is methyl.

10. A compound according to claim 9 having the following NMR spectrum:
NMR (d$_6$-DMSO) 0.64–0.92 (9H, m, {CH$_3$}$_2$CHCH$_2$); 1.30 (3H, m, CH$_3$CH); 2.20–2.40 (2H, m, CH$_3$CH and CH$_3$CHCH); 2.45 (2H, m, ArCH$_2$); 2.55 (3H, d, J=4 Hz, NHCH$_3$); 3.68 (3H, s, OCH$_3$); 4.45 (1H, m, ArCH$_2$CH); 6.80 and 7.16 (4H, two d's, J=7 Hz, aromatic); 7.72 (1H, m, NHCH$_3$); 8.18 (1H, d, J=7 Hz, CONHCH$_3$); 8.72 (1H, s, NHOH {D$_2$O exchange}); 10.37 (1H, s, NHOH {D$_2$O exchange}).

11. A method of promoting an antiarthritic effect in a mammal in need thereof comprising administering thereto a collagenase inhibiting effective amount of a compound according to claim 1.

* * * * *